United States Patent [19]
O'Neill et al.

[11] Patent Number: 5,620,418
[45] Date of Patent: *Apr. 15, 1997

[54] RETROGRADE CORONARY SINUS CATHETER

[75] Inventors: William G. O'Neill, Ann Arbor; Nelson L. Huldin, Pittsfield Township, both of Mich.; Sheila J. Hanson, Mequon, Wis.; Walter L. Carpenter, McHenry, Ill.

[73] Assignee: Minnesota Mining and Manufacturing Company, St. Paul, Minn.

[ * ] Notice: The term of this patent shall not extend beyond the expiration date of Pat. No. 5,395,331.

[21] Appl. No.: 350,649

[22] Filed: Dec. 7, 1994

Related U.S. Application Data

[63] Continuation of Ser. No. 21,526, Feb. 23, 1993, Pat. No. 5,395,331, which is a continuation-in-part of Ser. No. 874,589, Apr. 27, 1992, Pat. No. 5,324,260.

[51] Int. Cl.$^6$ .................................................. A61M 29/00
[52] U.S. Cl. ............................................. 604/96; 606/194
[58] Field of Search ............................ 604/96–101, 103; 606/191, 192, 194

[56] References Cited

U.S. PATENT DOCUMENTS

| | | | |
|---|---|---|---|
| 1,049,087 | 12/1912 | Hill . | |
| 1,190,179 | 4/1916 | Livingston . | |
| 1,289,106 | 12/1918 | Bullock . | |
| 2,308,484 | 1/1943 | Auzin | 18/58 |
| 2,701,559 | 2/1955 | Cooper | 128/2 |
| 2,927,584 | 3/1960 | Wallace | 128/349 |
| 2,983,512 | 5/1961 | Fleischer | 273/72 |
| 3,344,791 | 10/1967 | Foderick | 128/349 |
| 3,385,300 | 5/1968 | Holter | 128/348 |
| 3,635,223 | 1/1972 | Klieman | 128/348 |
| 3,813,729 | 6/1974 | Szabo et al. | 16/119 |

(List continued on next page.)

FOREIGN PATENT DOCUMENTS

| | | | |
|---|---|---|---|
| 0204218 | 12/1986 | European Pat. Off. | A61M 25/00 |
| 0231601 | 8/1987 | European Pat. Off. | A61M 29/00 |
| 0249338 | 12/1987 | European Pat. Off. | A61M 25/00 |
| 0280225 | 8/1988 | European Pat. Off. | A61M 25/00 |
| 0299622 | 1/1989 | European Pat. Off. | A61M 25/00 |
| 0303757 | 2/1989 | European Pat. Off. | A61M 25/00 |
| 0416662 | 3/1991 | European Pat. Off. | A61M 25/04 |
| 2607706 | 6/1988 | France | A61M 5/14 |
| 3326648 | 2/1985 | Germany | A61M 29/00 |
| WO89/10155 | 11/1989 | WIPO | A61M 25/00 |
| WO95/32756 | 12/1995 | WIPO | A61M 25/04 |

OTHER PUBLICATIONS

Shanebrook et al.; "Vortex mixing catheter"; Medical & Biological Engineering & Computing; vol. 30 (1992) Jan., No. 1, pp. 123–124.

Advertisement entitled "Together we bring medical innovations to the world" (2 pages); from The Annals of Thoracic Surgery, vol. 56, No. 6, Dec. 1993 (DLP, Inc.).

Brochure entitled "Instructions for Use: Retroplegia Cannula" from Research Medical, Inc. (4 pages) Nov. 25, 1991.

Directions for Use: Retrograde Coronary Sinus Perfusion Cannula; DLP, Inc. (1990).

(List continued on next page.)

*Primary Examiner*—Corrine M. McDermott
*Attorney, Agent, or Firm*—Gary L. Griswold; Walter N. Kirn; Stephen W. Bauer

[57] ABSTRACT

A coronary sinus catheter for the retrograde infusion of cardioplegia solutions into the coronary sinus. The catheter is adapted for improved retention in the coronary sinus. The catheter comprises a catheter tube having infusion, pressure-sensing and balloon-inflation lumens, an inflatable balloon and a pressure sensor tube in fluid communication with the balloon-inflation lumen for sensing pressure in the inflatable balloon. The internal volume of the pressure sensor tube is relatively non-expansible relative to the internal volume of the inflation balloon in normal operation of the catheter. The balloon includes a plurality of segmented annular ribs.

85 Claims, 4 Drawing Sheets

U.S. PATENT DOCUMENTS

| | | | |
|---|---|---|---|
| 3,815,608 | 6/1974 | Spinosa et al. | 128/349 |
| 3,970,090 | 7/1976 | Loiacono | 128/349 |
| 4,351,341 | 9/1982 | Goldberg et al. | 128/348 |
| 4,465,072 | 8/1984 | Taheri | 128/348.1 |
| 4,531,936 | 7/1985 | Gordon | 604/49 |
| 4,552,558 | 11/1985 | Muto | 604/100 |
| 4,648,384 | 3/1987 | Schmukler | 128/1 |
| 4,689,041 | 8/1987 | Corday et al. | 604/53 |
| 4,721,109 | 1/1988 | Healey | 128/334 |
| 4,753,637 | 6/1988 | Horneffer | 604/53 |
| 4,762,130 | 8/1988 | Fogarty et al. | 128/348.1 |
| 4,782,834 | 11/1988 | Maguire et al. | 128/344 |
| 4,850,969 | 7/1989 | Jackson | 604/96 |
| 4,898,168 | 2/1990 | Yule | 128/207 |
| 4,927,412 | 5/1990 | Menasche | 604/96 |
| 4,931,330 | 6/1990 | Stier et al. | 428/40 |
| 4,934,996 | 6/1990 | Mohl et al. | 600/17 |
| 4,957,485 | 9/1990 | Andersson et al. | 604/96 |
| 5,009,662 | 4/1991 | Wallace et al. | 606/192 |
| 5,021,045 | 6/1991 | Buckberg et al. | 604/53 |
| 5,024,668 | 6/1991 | Peters et al. | 606/194 |
| 5,031,613 | 7/1991 | Smith et al. | 128/207 |
| 5,033,998 | 7/1991 | Corday et al. | 600/18 |
| 5,041,093 | 8/1991 | Chu | 604/104 |
| 5,091,205 | 2/1992 | Fan | 427/2 |
| 5,112,305 | 5/1992 | Barath et al. | 604/96 |
| 5,158,545 | 10/1992 | Trudell et al. | 604/53 |
| 5,173,346 | 12/1992 | Middleton | 428/53 |
| 5,180,368 | 1/1993 | Garrison | 604/104 |
| 5,196,024 | 3/1993 | Barath | 606/159 |
| 5,197,952 | 3/1993 | Marcadis et al. | 604/96 |
| 5,201,706 | 4/1993 | Noguchi et al. | 604/96 |
| 5,226,427 | 7/1993 | Buckberg et al. | 128/772 |
| 5,295,994 | 3/1994 | Bonutti | 606/192 |
| 5,308,325 | 5/1994 | Quinn et al. | 604/96 |
| 5,324,260 | 6/1994 | O'Neill et al. | 604/96 |
| 5,385,548 | 1/1995 | Williams et al. | 604/96 |
| 5,423,745 | 6/1995 | Todd et al. | 604/53 |
| 5,423,851 | 6/1995 | Samuels | 606/198 |
| 5,487,730 | 1/1996 | Marcadis et al. | 604/96 |
| 5,505,698 | 4/1996 | Booth et al. | 604/96 |

OTHER PUBLICATIONS

Pages 8 and 9 from Research Medical, Inc. (RMI) annual report; reporting (among other things) "Patent Pending—Textured Retrograde Cardioplegia Balloon Surface" and Patent Pending—Retracta-Guard™ Retention Lumen for Cardioplegia Balloon Catheters.

Leaflet on Surgitek Venous Cannula for cardiovascular bypass surgery.

Brochure entitled "Looking for a Retrograde Cardioplegia Cannula with a Manually–Inflated, Textured Silicone Balloon?" (1 pg.) Research Medical, Inc.

Brochure entitled "Retroplegia II—Coronary Sinus Cardioplegia Cannula with Retractaguard—Anti-Retraction Lumen" (2 pgs.) Research Medical, Inc.

Brochure entitled "Retroplegia with Textured Balloon" (2 pgs.) Research Medical, Inc.

Pages 12–14 from price listing of Research Medical, Inc. for Retroplegia Retrograde Cardioplegia.

Advertisement entitled "Introducing the Only ULTRA-SIL"; DLP (no date).

Leaflet (3 pgs.) from USCI entitled "USCI 1967–68–Cardiology Radiology Surgery and Accessories".

Leaflet (3 pgs.) from American Cystoscope Makers, Inc. (ACMI) entitled "Catheters and Related Products".

Menasche et al.; "La cardioplegie retrograde par le sinus coronaire"; Technique Chirurgicale; La Presse Medicale, 29 Nov. 1986 15, No. 42; pp. 2113–2114.

Zombolas et al.; "Retrograde coronary sinus perfusion: pressure monitoring"; Perfusion 1992; 7: 291–294.

Zombolas et al.; "Retrograde coronary sinus perfusion: pressure monitoring"; Perfusion 1992; 7:291–294.

Advertisement entitled "DLP Introduces the New Retrograde Coronary Sinus Perfusion Cannula"; DLP Inc. (1 page) Journal of Thoracic & Cardiovascular Surg. (Nov. 1992).

"Retroplegia® with Textured Balloon"; Research Medical, Inc., dated 1992.

Farcot et al.; "New Catheter–Pump System for Diastolic Synchronized Coronary Sinus Retroperfuson"; Medical Progress Through Technology; pp. 29–37 (1980).

Brochure entitled "Coronary Perfusion/Cardioplegia Infusion Cannulae" of Polystan A/S, Copenhagen, Denmark (undated).

One page leaflet with Retrograde Coronary Sinus Perfusion Cannula and Pressure Sensing Syringe of DLP (undated).

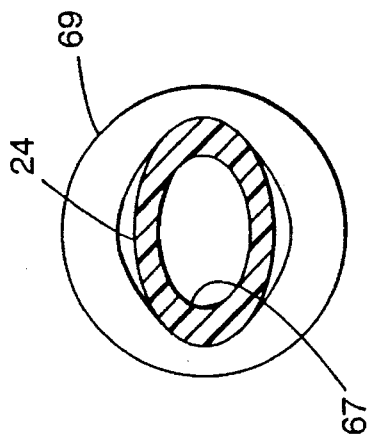
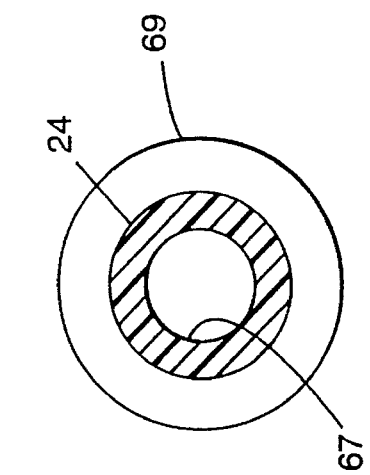
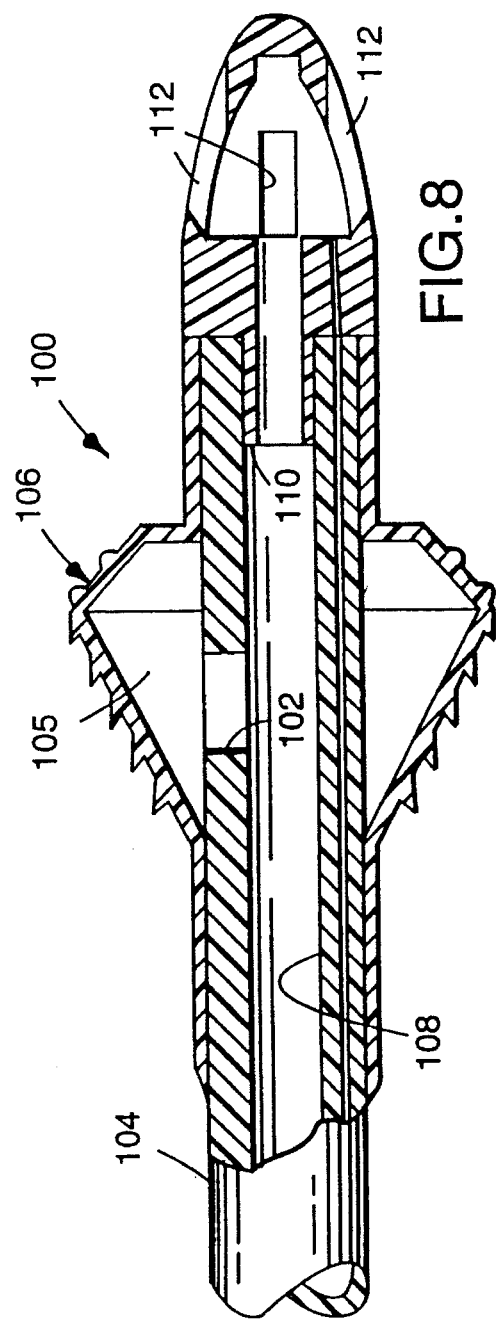

RETROGRADE CORONARY SINUS CATHETER

This is a continuation of application Ser. No. 08/021,526, filed Feb. 23, 1993, now U.S. Pat. No. 5,395,331 which is a continuation-in-part of application Ser. No. 07/874,589, filed Apr. 27, 1992, now U.S. Pat. No. 5,324,260.

BACKGROUND OF THE INVENTION

This invention relates generally to a coronary sinus catheter, and more particularly to a balloon catheter useful in the retrograde administration of cardioplegia through the coronary sinus.

Cardioplegia is a commonly used technique for protecting the heart during heart surgery. Typically, cooled cardioplegia solution (e.g., a potassium solution) is administered to the patient's heart in the antegrade direction through the patient's aorta. "Antegrade" refers to the direction of normal blood flow, and "retrograde" refers to the direction opposite of normal blood flow. The cardioplegia solution stops the heart and reduces its temperature to minimize damage to the heart during surgery.

In recent years, there has been increasing interest in administering cardioplegia in the retrograde direction (opposite of normal blood flow) via the coronary sinus. Such retrograde cardioplegia has been used with patients having critical coronary artery stenosis making diffusion of cardioplegia in the antegrade direction difficult and inefficient, and with patients suffering aortic valve disease. P. Menasche et al., "Retrograde Coronary Sinus Perfusion: A Safe Alternative for Ensuring Cardioplegic Delivery in Aortic Valve Surgery", The Annals of Thoracic Surgery, Vol. 34, No. 6, pages 647–658 (December 1982). See, also, J. Solorzano et al., "Retrograde Coronary Sinus Perfusion for Myocardial Protection during Cardiopulmonary Bypass", The Annals of Thoracic Surgery, Vol. 25, No. 3, pages 201–208 (March 1978); and D. Lolley et al., "Myocardial Distribution of Asanguineous Solutions Retroperfused under Low Pressure through the Coronary Sinus", J. Cardiovascular Surg., 21:287–294 (1980).

One difficulty in administering cardioplegia via the coronary sinus is that the sinus walls are slippery, extensible and are tapered such that the sinus vessels become smaller in the direction in which a catheter is advanced into the sinus vessel. See, e.g., U.S. Pat. No. 4,927,412, at column 1, lines 7–23. Techniques that have been developed to help secure balloon catheters in the coronary sinus include having someone manually hold the catheter in position during the surgery, or tying the catheter in position with a purse-string suture.

Dislodgement of such balloon catheters has been a long-standing issue with cardiovascular surgeons, which has even limited acceptance of the retrograde procedure. Acceptance of one fairly new technique, the continuous administration of "warm" cardioplegia, has been limited due to concerns regarding the ability of currently available catheters to stay in place in the coronary sinus. Dislodgement of the catheter during administration of warm cardioplegia may go undetected with potentially serious consequences.

U.S. Pat. No. 4,927,412 (Menasche) discloses a coronary sinus catheter for use in administering cardioplegia solution in the retrograde direction via the coronary sinus. That catheter includes an elongate member, and a balloon mounted on the elongate member. The elongate member has at least two lumens including one lumen in fluid communication with the interior of the balloon. The balloon includes at least one truncated conical surface having outwardly-facing spaced-apart parallel concentric lands formed thereon for frictionally engaging the coronary sinus. That catheter does not include a pressure sensor on the balloon inflation line.

The balloon described in U.S. Pat. No. 4,927,412 (Menasche) is formed of silicone rubber having a hardness of approximately 50 on the Shore A scale. The lands of that balloon are generally hemispherical in cross section having a radius of approximately 0.015 inches (0.038 millimeters), and are spaced apart a distance of approximately 0.05 inches (1.27 millimeters). The wall thickness of that balloon is approximately 0.030 inches (0.762 millimeters).

The balloon described in U.S. Pat. No. 4,927,412 (Menasche) was particularly designed for use with an open atrium technique. In the "open atrium" technique, the right atrium of the heart is substantially opened up with a large incision (e.g., two inches (50 mm)) so that direct access is provided to the coronary sinus. The distal end of the retrograde catheter is then inserted directly into the coronary sinus and the balloon is inflated to engage the walls of the coronary sinus.

While there are some advantages to the open atrium technique, one disadvantage is the inability to use a "Two-stage" venous catheter to drain the inferior vena cava and the right atrium. "Two-stage" venous catheters are sold under the trade designation "SARNS Two-Stage Venous Return Catheter" by Minnesota Mining and Manufacturing Company, St. Paul, Minn. Such "Two-stage" catheters are inserted through a small incision into the right atrium until the smaller diameter distal end portion of the catheter is positioned in the inferior vena cava. The smaller diameter, distal portion of the "Two-stage" catheter drains venous blood from the inferior vena cava, and the larger diameter portion, which is immediately proximal the distal portion, drains blood from the right atrium. The drained blood is then supplied to the extracorporeal support circuit, where among other things it is oxygenated before being returned to the patient. In the "open atrium" technique, two catheters (in addition to the retrograde catheter) must be used to perform the same function as the "Two-stage" venous catheter.

Many surgeons prefer to use a "blind" procedure as opposed to the "open atrium" technique. Only a small incision is made to gain access to the right atrium and the coronary sinus with the "blind" technique. Advantages of the "blind" procedure include making a smaller incision and allowing the use of the "Two-stage" venous catheter. The balloon thickness and durometer specified in U.S. Pat. No. 4,927,412 result in a balloon that is stiff enough to be difficult to use in the blind technique.

DLP, Inc., Grand Rapids, Mich., and RMI, Inc., Salt Lake City, Utah, sell retrograde catheters under the trade designations "dlp Retrograde Coronary sinus Perfusion Cannula (Model Code No. 94015 (15 French))" and "RETROPLEGIA Coronary Sinus Perfusion Cannula (Catalog Nos. RCS-014, RC-014-MIB and RC-014-MIBB)", respectively.

The "DLP" cannula comprises a wire-wound silicone rubber cannula body with a beveled tip. The DLP cannula includes an inflatable retention balloon mounted on the cannula body approximately ⅜ inches (10 mm) from the beveled tip, and an inflation assembly at the proximal end of the cannula for inflating the retention balloon. When not inflated, the "DLP" balloon has a very low profile and conforms fairly closely with the surface of the cannula body.

The DLP inflation assembly consists of an expandable balloon in fluid communication with the inflatable retention balloon, and a one-way valve between the expandable balloon and a luer fitting adapted to receive a fluid syringe for inflating the retention balloon. The arrangement is such that the expandable balloon, which is visible in use, is expanded when the inflatable retention balloon, which is inside the coronary sinus in use, is inflated. This provides an indication of pressure in the retention balloon. The visible/expandable "DLP" balloon has a wall thickness of approximately 0.019 inches (0.48 mm).

The "DLP" inflatable retention balloon, after being cut open, was measured to have a wall thickness of 0.019 inches (0.48 millimeters) when not inflated. From this figure, the inflated "DLP" retention balloon was calculated to have a wall thickness of approximately 0.006 inches (0.15 millimeters) when inflated.

RMI sells at least three retrograde cannulae including (1) a 14 French cannula with a "self-inflating/deflating" retention balloon and an insertion stylet (Catalog No. RCS-014); (2) a 14 French cannula with a manually inflatable balloon and a malleable stylet (Catalog No. RC-014-MIB); and (3) a 14 French cannula with a manually inflatable balloon and a "Buckberg" stylet (Catalog No. RC-014-MIBB).

The manually inflatable balloon of the "RMI" catheter sold under Catalog No. RC-014-MIB, after being cut open, was measured to have a wall thickness of 0.017–0.019 inches (0.43–0.48 millimeters) when not inflated. From this figure, the inflated "RMI" balloon was calculated to have a wall thickness of approximately 0.006 inches (0.15 millimeters) when inflated. Like the "DLP" balloon, that "RMI" balloon (Catalog No. RC-014-MIB) conforms fairly closely with the surface of the cannula when the balloon is not inflated.

One problem with both the "DLP" and "RMI" cannulae models with uninflated balloons that conform to the surface of the cannula is that the balloons when inflated tend to become displaced relative to the longitudinal axis of the cannula. This allows the distal end of the catheter to become displaced toward the walls of the coronary sinus.

U.S. Pat. No. 5,021,045, which may relate to RMI's "self-inflating/deflating" cannula sold under catalog No. RCS-014, describes a retrograde cannula having a retention balloon which is filled with the infusion fluid via openings between the infusion lumen and the interior of the balloon. That balloon is "constructed so that it is not necessary for the balloon to expand significantly from its unfilled state in order to seal the coronary sinus." See, e.g., column 9, lines 3–9, of U.S. Pat. No. 5,021,045. As reported in U.S. Pat. No. 5,021,045, that balloon is formed of polyurethane, and has a wall thickness within the range of 0.003–0.005 (0.004) inches (0.076–0.127 mm (0.102 mm)).

U.S. Pat. No. 5,021,045 also describes a particular ratio of cross-sectional areas between the infusion lumen outlets and the openings between the balloon and the infusion lumen, which among other things is apparently necessary in order for the balloon to be self-filling. While U.S. Pat. No. 5,021,045 discusses avoidance of "jet-like flow" exiting the catheter by regulating the above ratio and boring the infusion lumens at an angle, it has been found that the RMI cannulae sold under Catalog Nos. RCS-014 and RC-014-MIB spray a thin stream of fluid through each outlet for a distance of several inches when saline solution is delivered through the infusion lumen and the cannula is held in air.

SUMMARY OF THE INVENTION

This invention provides a coronary sinus catheter particularly useful for the retrograde administration of cardioplegia solution into the coronary sinus of a patient's heart; which is particularly adapted for improved retention and stability in the coronary sinus; which in one aspect is designed to measure and display temperature at the catheter; which in another aspect is adapted to show when a vacuum is drawn on a retention balloon mounted adjacent the distal end of the catheter; and which in yet another aspect is adapted to provide a gentle, non-spraying flow of cardioplegia solution.

The catheter of the invention is adapted for use in either the "blind" or "open atrium" techniques, and is designed to maintain the retention balloon co-centric with the longitudinal axis of the catheter.

Generally, a catheter of the invention comprises a flexible, elongate catheter tube having proximal and distal ends, an inflatable balloon for securing the distal end of the catheter in the coronary sinus, and a pressure sensor tube for sensing pressure in the balloon to indicate the status of the balloon. The catheter tube includes infusion, pressure-sensing and inflation lumens extending longitudinally through the tube. At least one infusion lumen outlet is provided generally adjacent the distal end of the catheter tube, and at least one pressure-sensing lumen outlet is provided generally adjacent the distal end of the catheter tube. The balloon is positioned on the catheter tube generally adjacent the distal end of the catheter tube but proximally of the infusion lumen and pressure-sensing lumen outlets. One end of the inflation lumen is in fluid communication with the interior of the balloon for inflating the balloon. The balloon is molded of elastomeric material having a durometer in the range of 20 to 35 on the Shore A scale, and has a wall thickness in the range of 0.3–0.5 millimeters when not inflated. The balloon has a plurality of outwardly-facing, spaced-apart, segmented, annular ribs or lands for frictionally engaging the coronary sinus.

One end of the pressure sensor tube is in fluid communication with the end of the inflation lumen opposite the inflation balloon. The pressure sensor tube is formed of elastomeric material having a durometer greater than 35 on the Shore A scale, and has a wall thickness greater than 0.6 millimeters. The internal volume of the pressure sensor tube is relatively non-expansible relative to the internal volume of the inflation balloon in normal operation of the catheter. A connection device is provided in fluid communication with the end of the pressure sensor tube opposite the inflation lumen for connecting a pressurizing means to the catheter to inflate and/or deflate the inflatable balloon.

Preferably, the pressure sensor tube has a durometer in the range of 35–50 on the Shore A scale, and a wall thickness in the range of 0.6–1.3 millimeters. Most preferably, the balloon has a wall thickness when not inflated of approximately 0.33–0.48 millimeters, and the pressure sensor tube has a wall thickness of approximately 0.76–1.01 millimeters.

According to one aspect of the invention, each segmented annular rib or land comprises a plurality of raised rib portions separated by non-raised portions, with the raised rib portions and non-raised portions extending annularly around the periphery of the balloon in alternating fashion. In one preferred version, the raised rib portions of adjacent ribs or lands are staggered such that the raised rib portions of one rib are generally longitudinally aligned with the non-raised portions of the adjacent rib or land. In another preferred version, the raised rib portions of generally adjacent ribs or lands are generally aligned in the longitudinal direction of the catheter, and the non-raised portions of generally adjacent ribs or lands are generally aligned in the longitudinal direction.

Preferably, the non-raised portions preferentially stretch in comparison with the raised rib portions as the balloon is inflated, thereby reducing stretching and distortion of the raised rib portions as the balloon is inflated.

Also, preferably, the raised rib portions have a generally asymmetrical profile along the longitudinal direction of the catheter, with the raised rib portions having an upper surface sloping smoothly and gradually forwardly to the surface of the balloon, and a back surface extending from the upper surface more steeply to the surface of the balloon than the upper surface slopes to the surface of the balloon.

These and other advantages and features will be pointed out hereinafter.

BRIEF DESCRIPTION OF THE DRAWING

The invention will be further described with reference to the drawing wherein corresponding reference characters indicate corresponding parts throughout the several views of the drawing, and wherein:

FIG. 4 is a cross-sectional view substantially along line 4—4 of FIG. 1, illustrating a pressure-sensing tube portion;

FIG. 5 is a cross-sectional view similar to FIG. 4 of the pressure-sensing tube portion, illustrating the cross section of the pressure-sensing tube portion when the balloon is drawn down by vacuum;

FIG. 8 is a longitudinal cross-sectional view similar to FIG. 3 illustrating an alternative, autoinflating embodiment of the balloon catheter;

FIG. 9 is a longitudinal cross-sectional view similar to FIGS. 3 and 8 but further cut away, illustrating yet another alternative embodiment of the balloon catheter;

DETAILED DESCRIPTION OF A PREFERRED EMBODIMENT

Figure 1:
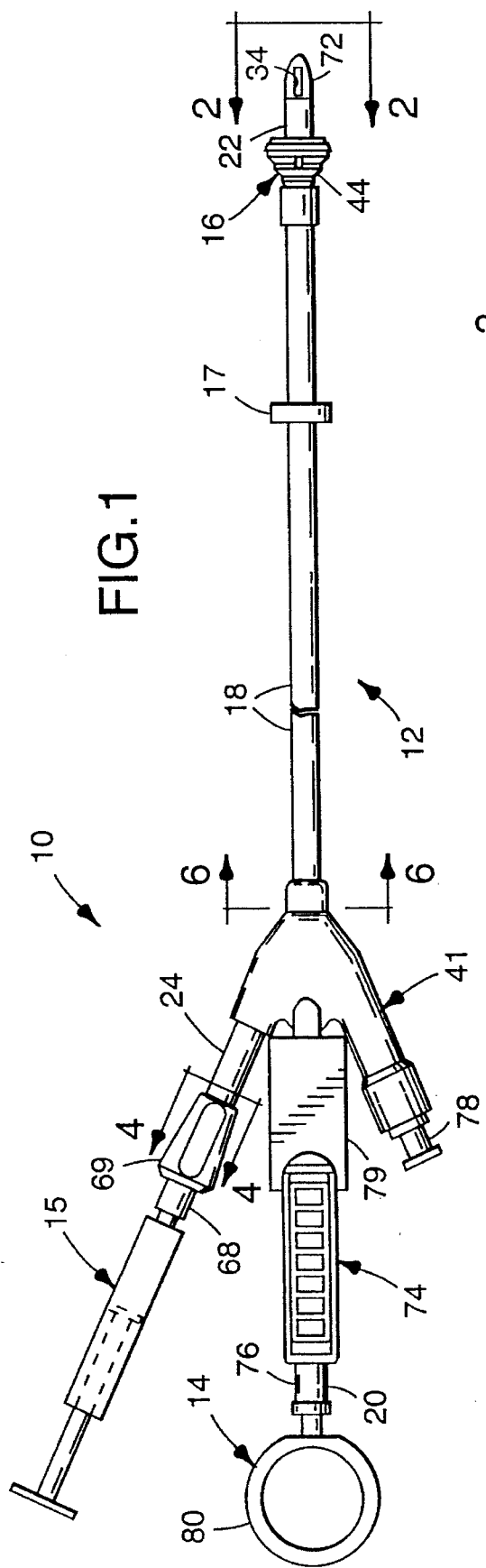
FIG. 1 is a side view of the retrograde coronary sinus catheter of the invention.
Figure 2:
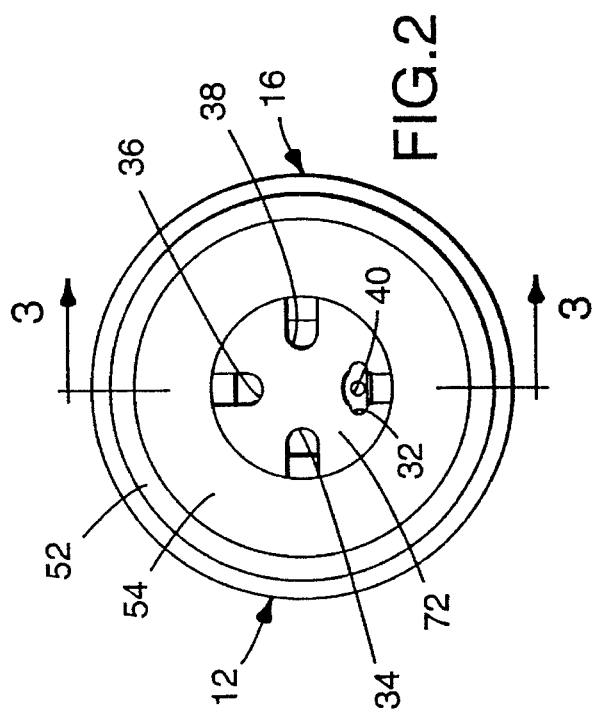
FIG. 2 is a distal end view of the catheter of FIG. 1.
Figure 6:
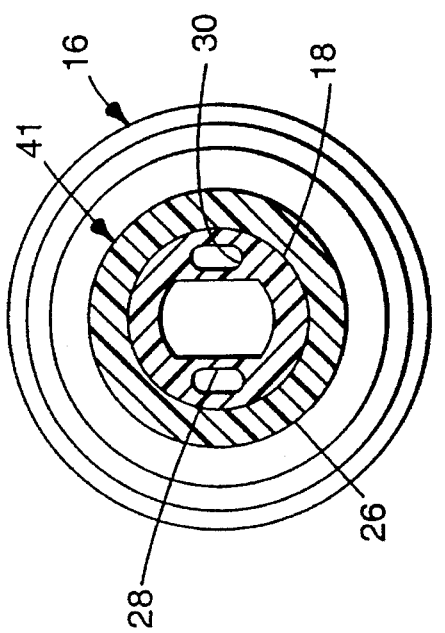
FIG. 6 is a cross-sectional view substantially along line 6—6 of FIG. 1.

Now referring to the drawing, a coronary sinus catheter assembly of the invention is indicated in its entirety by the reference numeral 10. The coronary sinus assembly 10 includes a coronary sinus catheter 12, a malleable stylet 14 and a syringe 15 for inflating an inflatable balloon 16 mounted on the catheter 12. A preferred stylet 14 is described in co-assigned U.S. patent application Ser. No. 08/238,416, filed Apr. 28, 1994, now U.S. Pat. No. 5,401, 244 which is a file wrapper continuation of Ser. No. 07/979, 010, filed Nov. 19, 1992 by Christopher M. Boyken and Thomas T. Vaalburg (incorporated herein by reference). An adjustable annular suture ring 17 may be provided along the catheter tube 18. The catheter 12 is a modified version of the catheter described in U.S. Pat. No. 4,927,412 (Menasche), which is incorporated herein by reference. The catheter 12 is particularly designed for the retrograde infusion of cardioplegia solution into the coronary sinus of a patient's heart. The catheter 12 is designed for use with either the "blind" or "open atrium" techniques.

As shown in FIG. 1, the catheter 12 generally comprises a flexible, elongate catheter tube 18 (e.g., 17 French) having proximal and distal ends 20 and 22, the inflatable balloon 16 which is adapted for retaining the distal end 22 of the catheter 12 in the coronary sinus, and a pressure or inflation sensor tube 24 for sensing pressure in the balloon 16 to indicate the status of the balloon 16. The pressure or inflation sensor tube 24 has an internal volume that is relatively non-expansible relative to the internal volume of the inflation balloon 16 in normal operation of the catheter 12.

As used herein, "proximal" and "distal" refer to opposite directions along the catheter 12. The "distal" direction is the direction (rightwardly in FIG. 1) toward the end 22 of the catheter 12 that is inserted in the coronary sinus. The "proximal" direction is the direction (leftwardly in FIG. 1) toward the end 20 of the catheter 12 which is connected to other components, such as tubing leading from a heat exchanger for cooling cardioplegia (not shown), of an extracorporeal support circuit (also not shown). Cardioplegia solution being delivered to the coronary sinus flows in the "distal" direction through the catheter 12. The proximal end of the catheter 12 will be indicated by the reference numeral 20.

The catheter tube 18 includes infusion, pressure-sensing and inflation lumens 26, 28 and 30 extending longitudinally through the catheter tube 18. At least one infusion lumen outlet, preferably four outlets 32, 34, 36 and 38, is/are provided generally adjacent the distal end 22 of the catheter tube 18. At least one pressure-sensing lumen outlet 40 is provided generally adjacent the distal end 22 of the catheter tube 18. One end of the pressure sensor tube 24 is in fluid communication with the proximal end of the inflation lumen 30, which is the end opposite the inflation balloon 16.

The catheter tube 18 is preferably formed of silicone rubber material, and is flexible and resilient. As an alternative, the catheter tube 18 can be of the wire-reinforced type, which although it will be stiffer than the preferred version would still be flexible and resilient in normal use.

A three-way Y-type connection assembly 41 is mounted on the proximal end 20 of the catheter tube 18 to adapt the catheter 12 for connecting (1) the syringe 15 in fluid communication with the balloon-inflation lumen 30, (2) a cardioplegia supply line (not shown) in fluid communication with the infusion lumen 26, and (3) a pressure sensing line (not shown) in fluid communication with the pressure-sensing lumen 28 to monitor pressure in the coronary sinus adjacent the distal tip 72 of the catheter 12.

The connection assembly 41 is molded of silicone material and is bonded to the catheter tube 18 by any suitable technique including silicone adhesive, such as available under the trade designation "LOCTITE 18188" from Loctite Corp., Newington, Conn. The pressure sensor tube 24 may be an integral molded part of the connection assembly 41.

The inflatable balloon 16 is mounted on the catheter tube 18 generally adjacent the distal end 22 of the catheter tube 18 proximally (leftwardly in FIG. 1) of the infusion lumen and pressure-sensing lumen outlets 32, 34, 36, 38 and 40. One end of the inflation lumen 30 is in fluid communication with the interior 42 of the balloon 16 for inflating the balloon 16. The balloon 16 has a generally pear-shaped cross-sectional profile along the longitudinal direction of the catheter tube 18.

The balloon 16 is molded of elastomeric material, such as silicone rubber, having a durometer in the range of 20 to 35 on the Shore A scale, and has a wall thickness in the range of 0.3–0.5 millimeters when not inflated. Most preferably, the balloon 16 has a wall thickness when not inflated of approximately 0.33–0.48 millimeters (e.g., 0.012–0.019 inches). For example, the wall thickness of the balloon 16 may be approximately 0.43 mm (0.017 inches), and the durometer is approximately 28 on the Shore A scale.

Suitable silicone rubber material for the balloon 16 includes a blend of the materials available under the trade designations "HE-26" and "HE-30" from Dow Corning Corp., Midland, Mich. The balloon 16 may be molded by using liquid injection molding (LIM), transfer molding or blow molding.

The balloon 16 has a plurality of concentric outwardly-facing spaced-apart parallel lands or ribs 44 for frictionally engaging the coronary sinus. The balloon's normal, uninflated configuration is expanded outwardly from the catheter tube 18 such that the longitudinal cross-sectional profile of the balloon 16 is generally pear-shaped. The balloon 16 may be drawn inwardly from its normal configuration when a vacuum is drawn on the inflation lumen 30. The pressure sensor tube 24 is adapted to provide an indication (among other things) of whether a vacuum has been drawn on the inflatable balloon 16. FIG. 5 illustrates the pressure sensor tube 24 flattening out somewhat in response to vacuum.

As used herein, "vacuum" merely refers to the pressure in the interior 42 of the balloon 16 being less than the outside ambient pressure or local environmental pressure (e.g., pressure in the right atrium or coronary sinus). Normally, it is used to refer to the interior pressure of the balloon 16 being sufficiently low that the balloon 16 is drawn toward the catheter tube 18.

It is believed that drawing the balloon 16 inwardly toward the catheter tube 18 facilitates introducing the distal end 22 of the catheter 12 into the coronary sinus via the "blind" technique. In the "blind" technique, a small incision is made into the right atrium of the heart and the distal end 22 of the catheter 12 is introduced into the coronary sinus "blind" via the right atrium. In the "open atrium" technique as opposed to the "blind" technique, a large incision is made into the right atrium to allow direct access of the coronary sinus.

The profile of the balloon 16 includes a substantially conical proximal surface 46 tapering gradually down in the proximal direction (leftwardly in FIG. 1) to the surface of the catheter tube 18, and a distal surface 48 tapering at a higher average slope down in the distal direction (rightwardly in FIG. 1) to the surface of the catheter tube 18 or the distal tip 72 of the catheter 12. The balloon 16 is generally symmetrical around the longitudinal axis of the catheter tube 18. The proximal surface 46 tapers downwardly at an included angle of approximately 50 degrees from the maximum radius of the balloon 16 to the surface of the catheter tube 18.

As used herein, "included angle" refers to the angle formed between opposite sides of the conical surfaces, and is double the angle formed between the conical surface and the longitudinal axis of the catheter tube 18.

The distal surface 48 of the balloon 16 includes two portions: (1) a first (conical or frustoconical) portion 52 extending distally from the proximal surface 46 and tapering in the distal direction at an included angle of approximately 80 degrees; and (2) a second generally flat portion 54 extending between the outer circumferential surface of the distal tip 72 or catheter tube 18 adjacent the distal tip 72. The flat portion 54 is generally perpendicular to the longitudinal axis of the catheter tube 18.

Figure 7:
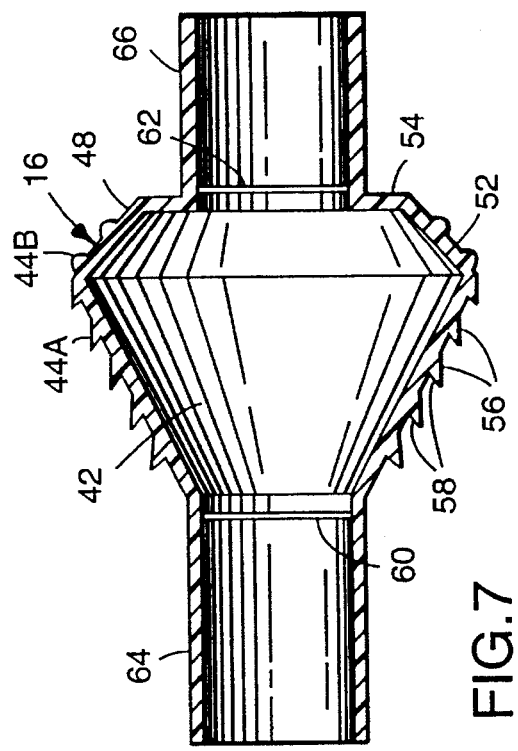
FIG. 7 is a longitudinal cross-sectional view through the inflatable balloon shown in FIGS. 1–2.

The annular ribs 44 are formed on the proximal surface 46 and the conical portion 52 of the distal surface 48 of the balloon 16. As illustrated in FIG. 7, the ribs 44A formed along the proximal surface 46 of the balloon 16 are asymmetrical. The proximal ribs 44A include generally annular, outer surface portions 56 that are co-axial with the longitudinal axis of the catheter tube 18, and proximal surface portions 58 extending outwardly from the proximal surface 46 approximately at a right angle to the proximal surface 46 to the annular, outer surface portions 56. The juncture between the annular, outer surface portions 56 and the proximal surface portions 58 has a suitable radius, such as 0.005 inches (0.127 mm). Most preferably, there are five ribs 44A formed along the distal surface 48 of the balloon 16, and the five ribs 44A are spaced at approximately 0.07 inch (1.78 mm) intervals in the longitudinal direction of the catheter 12.

The annular ribs 44B formed along the conical portion 52 of the balloon's proximal surface 46 are preferably generally symmetrical through their cross sections. The ribs 44B extend from the surface of the conical portion 52 approximately 0.02 inches (0.508 mm), and have a cross-sectional radius of approximately 0.03 inches (0.762 mm).

As shown in FIG. 7, the balloon 16 is provided with two annular glue rings 60 and 62 along tubular extensions 64 and 66, which serve to provide an even glue line between the tubular extensions 64 and 66 and the catheter tube 18. The even glue line is believed to help stabilize the balloon 16 to maintain the balloon 16 centered around the catheter tube 18 as the balloon 16 is inflated. Suitable glue includes a silicone adhesive available under trade designation "LOCTITE 18188" from Loctite Corp., Newington, Conn., or the silicone adhesive available under the trade designation "WALKER 950".

The pressure sensor tube 24 is formed of elastomeric material having a durometer greater than 35 on the Shore A scale, and having a wall thickness greater than 0.6 millimeters. Preferably, the pressure sensor tube 24 has a durometer in the range of 35–50 on the Shore A scale, and a wall thickness in the range of 0.6–1.3 millimeters (0.025–0.05 inches). Most preferably, the pressure sensor tube 24 has durometer of 40 on the Shore A scale, and a wall thickness of approximately 0.76–1.01 millimeters (0.03–0.04 inches). For example, the pressure sensor tube 24 may have a wall thickness of 0.89 millimeters (0.035 inches).

The pressure sensor tube 24 may conveniently be formed of silicone rubber material available under the trade designation "LSR 595" from Dow Corning Corp., Midland, Mich. by liquid injection molding ("LIM"), transfer molding or extrusion. The lumen 67 of the pressure sensor tube 24 may have a relaxed diameter (see FIG. 4) of approximately 0.25 inches (6.4 mm).

A connection device 68 is provided at the proximal end 20 of the catheter 12 in fluid communication with the proximal end of the pressure sensor tube 24, which is the end opposite the inflation lumen 30. The connection device 68 is adapted for connecting a pressurizing means, such as the syringe 15, to the catheter 12 to inflate and/or deflate the inflatable balloon 16.

The syringe 15 also permits a vacuum to be drawn on the balloon 16 as discussed above to draw the balloon 16 inwardly toward the catheter tube 18. The syringe 15 is preferably filled with saline solution, which is not compressible, although air could also be used. It is contemplated that the syringe would have an internal volume of 3 cc, and that up to 5 cc of fluid volume could be introduced into the balloon 16, inflation lumen 30 and pressure sensor tube 24.

A valve 69 is provided between the connection device 68 and the pressure sensor tube 24. The valve 69 is designed to prevent flow or escape of fluid through the valve 69, except when the male luer fitting of the syringe 15 is inserted into the connection device 69. When the luer fitting of the syringe 15 is mounted in the connection device 68, the valve 69 opens to allow delivery of fluid from the syringe 15 to the balloon 16 or withdrawal of fluid from the balloon 16 by drawing vacuum with the syringe 15. The valve 69 allows the syringe 15 to be withdrawn, with fluid being sealed in the balloon 16, inflation lumen 30 and pressure sensor tube 24.

In another preferred aspect of the invention, the infusion lumen 26 includes a constricted portion 70 (FIG. 3) spaced from the infusion lumen outlets 32, 34, 36 and 38. The total cross-sectional area of the infusion lumen outlet(s) 32, 34, 36 and 38 is substantially greater than the cross-sectional area of the constricted portion 70 of the infusion lumen 26 so that fluid exiting the infusion lumen outlets 32, 34, 36 and 38 is decelerated relative to its velocity through the constricted portion 70 of the infusion lumen 26. For example, the total cross-sectional areas of the infusion lumen outlets 32, 34, 36 and 38 may be approximately 16.8 mm$^2$; the cross-sectional area of the constricted portion 70 may be approximately 1.8 mm$^2$; and the typical cross-sectional area of the infusion lumen may be 3.25 mm$^2$.

Preferably, the molded distal tip 72 is soft and rounded-conical and has a closed end. As used herein, "rounded-conical" refers to a generally conical structure in which the surfaces may be smoothly rounded instead of tapering at a constant angle. The infusion lumen outlets 32, 34, 36 and 38 comprise a plurality of elongate outlet slots (also 32, 34, 36 and 38) formed in the distal tip 72. The elongate slots 32, 34, 36 and 38 are spaced approximately equally around the circumference of the distal tip 72. The pressure-sensing lumen outlet 40 opens into one of the elongate outlet slots 32. The distal tip 72 is conveniently molded of silicone rubber material having a durometer of approximately 50 on the Shore A scale.

The constricted portion 70 may be formed by a reduced diameter tubular extension of the molded distal tip 72 extending into the catheter tube 18. The inside diameter of the constricted portion 70 may be approximately 0.06 inches (1.52 mm). The internal space formed between the infusion lumen outlets 32, 34, 36 and 38 and the constricted portion 70 preferably has a cross-sectional area greater than the cross-sectional area of the constricted portion 70.

In yet another preferred aspect of the invention, a temperature sensing strip 74 (FIG. 1) is provided along the infusion lumen 26 generally adjacent the proximal end 23 of the catheter 12. The temperature sensing strip 74 includes liquid crystal display means (also 74) on the catheter 12 for displaying the temperature of the fluid being infused. Preferably, duplicate display means 74 are provided along opposite sides of the catheter 12. Temperature sensing strips of suitable type are available from American Thermometer Co., Glenview, Ill. It is believed that the temperature sensing strip 74 will be a significant convenience for the surgeon, allowing direct reading of the temperature of the cardioplegia solution without looking away from the surgical field.

The temperature sensing strip 74 conveniently has an operating range between 4–40 degrees Celsius. A plurality of indicia may be provided on the temperature sensing strip 74 to indicate various temperature points. The indicia on the strip 74 may be of the type comprising a plurality of small sections of temperature sensitive material arranged along the temperature sensing strip 74 which change color according to their temperature.

For example, seven sections corresponding to temperature values of 4, 7, 10, 13, 34, 37 and 40 degrees Celsius could be provided on each display means 74. The sections corresponding to 4, 7, 10 and 13 degree Celsius values are framed by the color blue, and the sections corresponding to 34, 37 and 40 degrees are framed by the color red. If the temperature is exactly 10 degrees Celsius, the 10 degree Celsius section would turn a bright turquoise color. A straw color in that section would indicate a temperature slightly above the value displayed in that small section, and a royal blue color in that section would indicate a temperature slightly below the value displayed.

A suitable connection device 76 is provided on the proximal end 23 of the temperature sensing strip 74 for connecting a cardioplegia supply line (not shown) in fluid communication with the infusion lumen 26. For example, the connection device 76 may comprise a suitable locking female luer fitting 76. A similar connection device 78 (e.g., a locking female luer fitting 78) may be provided at the proximal end of the pressure-sensing lumen 28 for connecting a pressure sensing line (not shown) in fluid communication with the pressure-sensing lumen 28.

A clamp 79, such as a pinch clamp 79 of conventional design, is provided on the connection assembly 41 along the infusion lumen 26 between the catheter tube 18 and the temperature sensing strip 74. The clamp 79 allows manual control of cardioplegia solution flow through the catheter 12, as well as manual closing of the infusion lumen 26 to stop delivery of cardioplegia solution.

The stylet 14 includes malleable wire, and is deformable to set bends therein. Preferably, the stylet 14 is formed by coating the malleable wire with plastic material. As shown in FIG. 1, a ring 80 may be provided on the proximal end of the stylet 14 for grasping the stylet 14 with a finger, either for removal from the catheter 12 or to facilitate manipulating the catheter assembly 10 to insert the distal end 22 of the catheter 12 into the coronary sinus. The ring 80 may be molded of suitable plastic resin material.

As illustrated in FIG. 8, an alternative catheter designated generally 100 has at least one balloon-inflating opening 102 formed in the catheter tube 104 between the interior 105 of the balloon 106 and the infusion lumen 108. In this embodiment, a constricted portion 110, similar to constricted portion 70, is positioned along the infusion lumen 108 between the balloon-inflating opening 102 and the infusion lumen outlet 112. The constricted portion 110 is adapted to create back pressure in the infusion lumen 108 to automatically inflate the balloon 106 when fluid is being infused through the catheter 100. Other features of catheter 100 are similar to catheter 12 described above, with one exception being that catheter 100 lacks a separate inflation lumen.

As illustrated in FIG. 9, a second alternative catheter designated generally 200 has an inflatable balloon 202 which lays flat against the outer surface of the catheter tube 204 when the balloon 202 is not inflated. The balloon 202 is provided with a plurality (e.g., 4) of annular lands or ribs 206 that are similar in many respects to ribs 44A of balloon 16. The ribs 206 of this alternative embodiment are asymmetrical in a fashion similar to ribs 44A. Other features of catheter 200 are similar to catheter 12.

Figure 10:
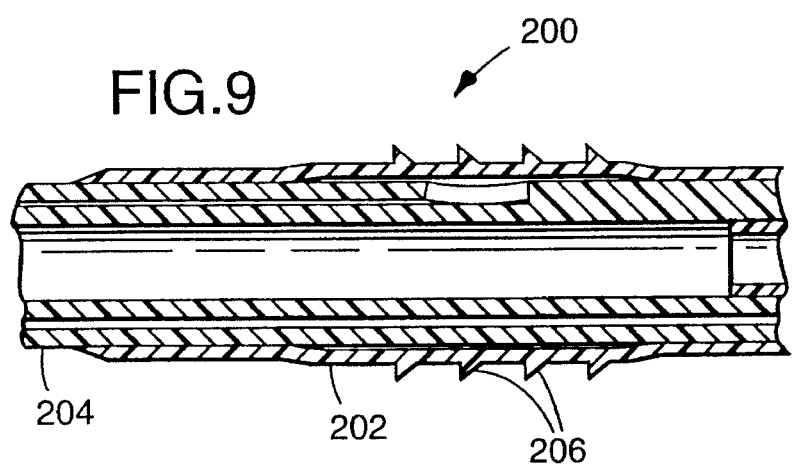
FIG. 10 shows the distal portion of another embodiment of the coronary sinus catheter.

FIG. 10 illustrates another embodiment of the coronary sinus catheter of the invention, here designated 300. The coronary sinus catheter 300 includes a balloon 302 having a plurality of outwardly-facing, spaced-apart, segmented, parallel, annular ribs or lands generally indicated at 304 for frictionally engaging the coronary sinus, but is otherwise similar to the catheter 200 in FIG. 9. As an alternative, the segmented-rib balloon catheter could be formed in the profile of FIG. 1, 3, 7 and 8, and be of the type including a balloon-inflating opening, similar to the embodiment of FIG. 8, that allows infusion fluid to inflate the balloon 302.

The segmented ribs or lands are preferably integrally molded with the balloon 302 of generally elastomeric silicone material. Each segmented rib or land 304 comprises a plurality of solid raised rib portions 306 separated by non-raised portions 308, with the raised rib portions 304 and non-raised portions 308 extending annularly around the balloon 302 in alternating fashion. The raised rib portions 306 of adjacent ribs or lands 304 are generally aligned along the longitudinal direction of the catheter 300, and the non-raised portions 308 of adjacent ribs or lands 304 are generally aligned along the longitudinal direction of the catheter 300.

The balloon 302 preferable is expandable from an un-inflated diameter (FIG. 10), generally equal to the diameter of the catheter tube and closely conforming to the catheter tube, to an inflated diameter (not shown), substantially greater than the diameter of the catheter tube. The balloon 302 is at its un-inflated diameter for introducing the catheter 300 into the coronary sinus, and is inflated to its inflated diameter to secure the distal end of the catheter 300 in the coronary sinus.

Preferably, the non-raised portions 308 preferentially stretch in comparison to the raised rib portions 306 as the balloon 302 is inflated. The arrangement is such as to reduce stretching and distortion of the raised rib portions 306 to help them maintain, or reduce distortion from, their original profile as the balloon 302 is inflated.

Also, preferably, the raised rib portions 306 have a generally asymmetrical profile along the longitudinal direction of the catheter 300. The raised rib portions 306 have an upper surface 310 sloping smoothly and gradually forwardly to the surface of the balloon 302, and a back surface 312 extending from the upper surface 310 more steeply to the surface of the balloon 302 than the upper surface 310 slopes to the surface of the balloon 302.

Most preferably, three to seven (e.g., six) segmented ribs or lands 304 are provided on the balloon 302. Four segmented ribs or lands 304 are shown in FIG. 10. Each segmented rib or land 304 has the same number of raised rib portions 306 and non-raised portions 308 as the other ribs or lands 304. For example, each segmented rib or land 304 may include eight raised rib portions 306, and eight non-raised portions 308.

Figure 3:
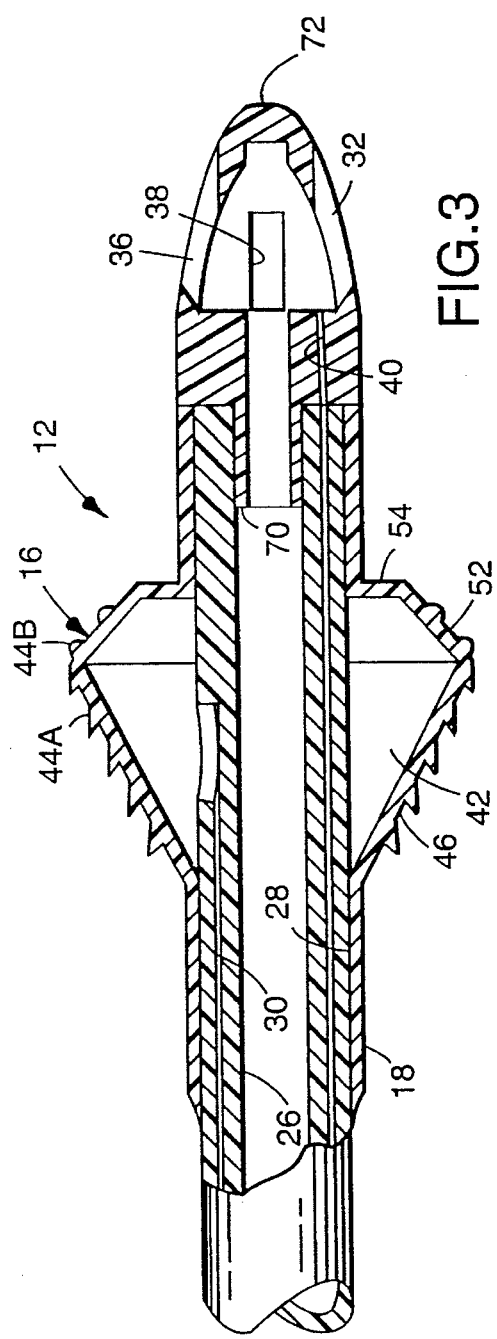
FIG. 3 is a longitudinal cross-sectional view of a distal end portion of the catheter of FIGS. 1 and 2 taken substantially along line 3—3 in FIG. 2.

FIG. 10 also illustrates a pressure sensing lumen outlet 314 extending out through the circumference of the catheter 300 as opposed to into a infusion lumen outlet as illustrated in FIG. 3.

Figure 11:
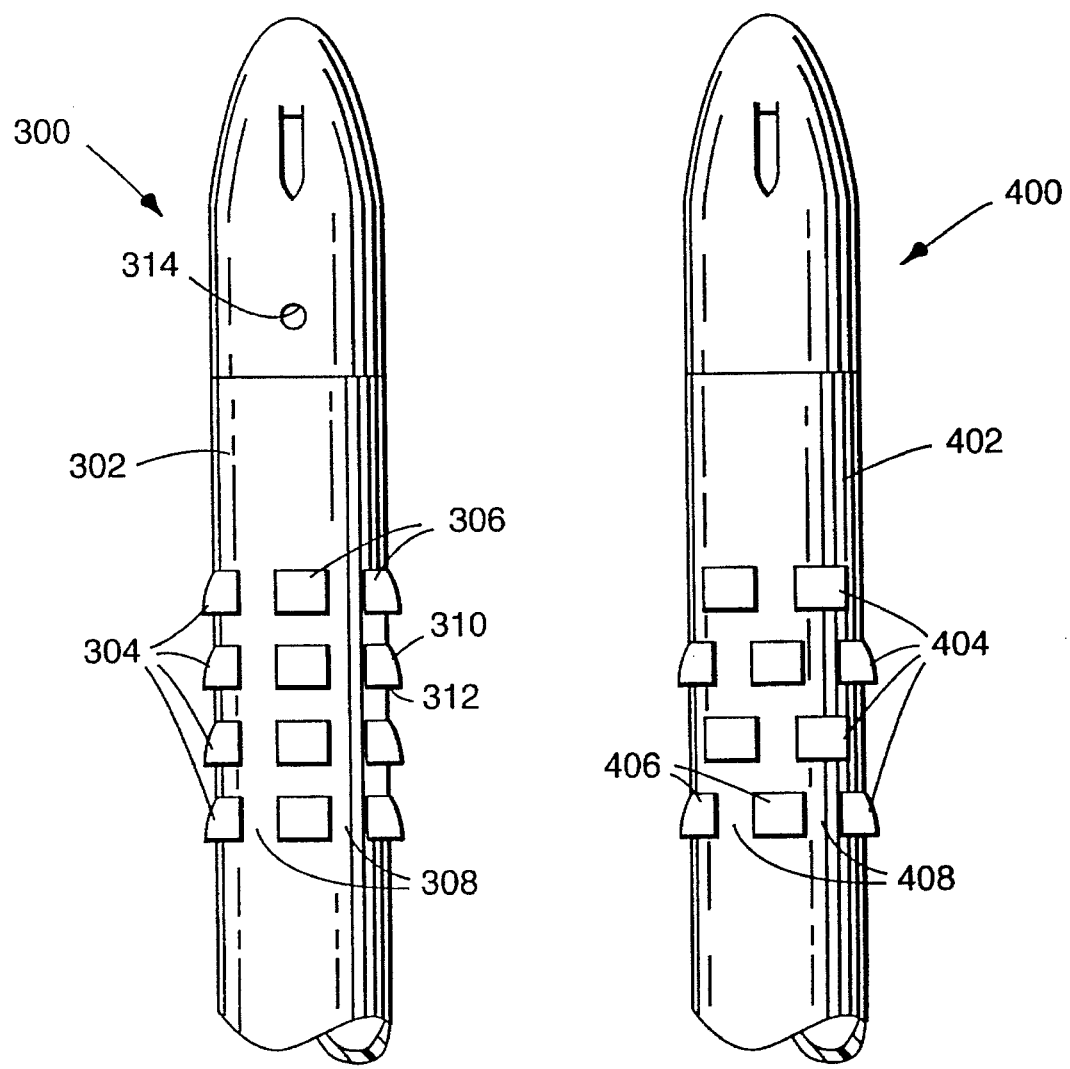
FIG. 11 shows the distal portion of yet another embodiment of the coronary sinus catheter, similar in some respects to the catheter of FIG. 10.

FIG. 11 illustrates yet another embodiment of the coronary sinus catheter, here designated 400, similar in many respects to catheter 300 shown in FIG. 10. Like catheter 300, the coronary sinus catheter 400 comprises a balloon 402 having segmented ribs or lands 404 formed by a plurality of raised rib portions 406 and non-raised portions 408 extending in alternating fashion around the periphery of the balloon 402. In contrast to catheter 300, the raised rib portions 406 of adjacent ribs or lands 404 are staggered such that the raised rib portions 406 are generally longitudinally aligned with the non-raised portions 408 of the adjacent rib or land 404.

The generally elongate raised rib portions 306 or 406 have a direction of elongation extending generally circumferentially along the balloon 302 or 402. As illustrated in FIGS. 10 and 11, the raised rib portions 306 or 406 have a length along their direction of elongation longer than the distance between adjacent raised rib portions 306 or 406 along the non-raised portion 308 or 408 separating the adjacent raised rib portions 306 or 406.

Also, as illustrated in FIGS. 10 and 11, the raised rib portions 306 or 406 of one segmented rib or land 304 or 404 each have a length along their direction of elongation generally equal to the other raised rib portions 306 or 406 of that segmented rib or land 304 or 404. The non-raised portions 308 or 408 of one segmented rib or land 304 or 404 each define a distance between adjacent raised rib portions 306 or 406 generally equal to the distance between raised rib portions 306 or 406 defined by the other non-raised portions 308 or 408 of that segmented rib or land 304 or 404.

OPERATION

To insert the catheter 12 into the heart via the "blind" technique, the right atrium is sutured and the distal end 22 of the catheter 12 (with the stylet 14 therein) is inserted through a small incision (in the area defined by the suture) into the right atrium. By placing a finger at the junction of the inferior vena cava and the atrio-ventricular groove, the distal end 22 of the catheter 12 can be guided into the coronary sinus. It may be helpful to gently lift the diaphragmatic aspect of the right ventricle to unfold the coronary sinus. The position of the catheter tip 72 can be verified by palpating the tip.

The balloon 16 should be inflated slowly with approximately 3 cc of saline solution, the stylet 14 removed from the catheter 12, and the pinch clamp 79 closed. The suture can then be tightened and the catheter 12 secured. The pinch clamp 79 may then be opened, all air removed, and lines attached to the connection device 76 for the infusion lumen 26 and the connection device 78 for the pressure-sensing lumen 28.

Cardioplegia solution may then be infused into the coronary sinus through the catheter 12. The pressure in the coronary sinus should be carefully monitored. Due to the deceleration of fluid after passing the constricted portion 72, flow through the infusion lumen outlets 32, 34, 36 and 38 is gentle and non-spraying. The surgeon may directly view the temperature sensing strip 74 to determine the temperature of the cardioplegia solution, or to verify information provided orally by the perfusionist.

As various changes could be made in the above constructions without departing from the scope of the invention, it is intended that all matter contained in the description above or shown in the accompanying drawing shall be interpreted as illustrative and not in a limiting sense.

We claim:

1. A coronary sinus catheter for the retrograde infusion of cardioplegia solution into the coronary sinus of a patient's heart, the catheter comprising:

a flexible, elongate catheter tube having proximal and distal ends and an outer diameter, and including at least an infusion lumen extending longitudinally through the tube, at least one infusion lumen outlet generally adjacent the distal end of the catheter tube, and means adjacent the proximal end of the catheter tube for connecting a source of cardioplegia solution to the catheter; and an inflatable balloon on the catheter tube generally adjacent the distal end of the catheter tube proximally of the infusion lumen outlet, the inflatable balloon being expandable as the balloon is inflated from an uninflated diameter, generally equal to the outer diameter of the catheter tube for introducing the catheter into the coronary sinus, to an inflated diameter, substantially greater than the outer diameter of the catheter tube for securing the distal end of the catheter in the coronary sinus;

the inflatable balloon having a plurality of outwardly-facing, spaced-apart, segmented, annular ribs or lands for frictionally engaging the coronary sinus, each segmented annular rib or land comprising a plurality of solid, raised, generally elongate rib portions separated by non-raised portions extending annularly around the periphery of the balloon in alternating fashion, the non-raised portions preferentially stretching in comparison to the raised rib portions as the balloon is inflated to its inflated diameter, the balloon, including the ribs or lands, being integrally molded of generally uniform elastomeric material; and the raised rib portions of adjacent ribs or lands being staggered such that the raised rib portions of one rib or land are generally longitudinally aligned with the non-raised portions of the adjacent rib or land.

2. A coronary sinus catheter according to claim 1 wherein:

the plurality of segmented ribs or lands comprises three to seven segmented ribs or lands;

each segmented rib or land having the same number of raised rib portions and non-raised portions as the other ribs or lands; and the raised rib portions having a generally asymetrical profile along the longitudinal direction of the catheter, the raised rib portions having an upper surface sloping smoothly and gradually forwardly to the surface of the balloon, and a back surface extending from the upper surface more steeply to the surface of the balloon than the upper surface slopes to the surface of the balloon.

3. A coronary sinus catheter according to claim 1 wherein the segmented ribs or lands are integrally molded with the balloon of silicone material constituting the elastomeric material.

4. A coronary sinus catheter according to claim 3 wherein:

the balloon has a wall thickness when not inflated of approximately 0.33–0.48 millimeters.

5. A coronary sinus catheter for the retrograde infusion of cardioplegia solution into the coronary sinus of a patient's heart, the catheter comprising:

a flexible, elongate catheter tube having proximal and distal ends and an outer diameter, and including at least an infusion lumen extending longitudinally through the tube, at least one infusion lumen outlet generally adjacent the distal end of the catheter tube, and means adjacent the proximal end of the catheter tube for connecting a source of cardioplegia solution to the catheter; and an inflatable balloon on the catheter tube generally adjacent the distal end of the catheter tube proximally of the infusion lumen outlet, the inflatable balloon being expandable as the balloon is inflated from an uninflated diameter, generally equal to the outer diameter of the catheter tube for introducing the catheter into the coronary sinus, to an inflated diameter, substantially greater than the outer diameter of the catheter tube for securing the distal end of the catheter in the coronary sinus;

the inflatable balloon having a plurality of outwardly-facing, spaced-apart, segmented, annular ribs or lands for frictionally engaging the coronary sinus, each segmented annular rib or land comprising a plurality of solid, raised, generally elongate rib portions separated by non-raised portions extending annularly around the periphery of the balloon in alternating fashion, the non-raised portions preferentially stretching in comparison to the raised rib portions as the balloon is inflated to its inflated diameter, the balloon, including the ribs or lands, being integrally molded of generally uniform elastomeric material; and the generally elongate raised rib portions having a direction of elongation extending generally circumferentially along the balloon.

6. A coronary sinus catheter according to claim 1 wherein the raised rib portions of adjacent ribs or lands are generally aligned along the longitudinal direction of the catheter.

7. A coronary sinus catheter according to claim 5 wherein the raised rib portions have a length along their direction of elongation longer than the distance between adjacent raised rib portions along the non-raised portion separating the adjacent raised rib portions.

8. A coronary sinus catheter according to claim 7 wherein the raised rib portions of one segmented rib or land each have a length along their direction of elongation generally equal to the other raised rib portions of that segmented rib or land.

9. A coronary sinus catheter according to claim 8 wherein the non-raised portions of one segmented rib or land each define a distance between adjacent raised rib portions generally equal to the distance between raised rib portions defined by the other non-raised portions of that segmented rib or land.

10. A coronary sinus catheter according to claim 9 wherein the catheter tube further defines a pressure lumen having lumen outlet generally adjacent the distal end of the catheter tube.

11. A coronary sinus catheter according to claim 10 wherein the balloon is formed of polymeric material having a Shore A hardness of between approximately 20 and 35.

12. A coronary sinus catheter according to claim 11 wherein the balloon is formed of silicone material.

13. A coronary sinus catheter for the retrograde infusion of cardioplegia solution into the coronary sinus of a patient's heart, the catheter comprising:

a flexible, elongate catheter tube having proximal and distal ends and an outer diameter, and including at least an infusion lumen extending longitudinally through the tube, at least one infusion lumen outlet generally adjacent the distal end of the catheter tube, and means adjacent the proximal end of the catheter tube for connecting a source of cardioplegia solution to the catheter; and an inflatable balloon on the catheter tube generally adjacent the distal end of the catheter tube proximally of the infusion lumen outlet, the inflatable balloon being expandable as the balloon is inflated from an uninflated diameter, generally equal to the outer diameter of the catheter tube for introducing the catheter into the coronary sinus, to an inflated diameter, substantially greater than the outer diameter of the catheter tube for securing the distal end of the catheter in the coronary sinus;

the inflatable balloon having a plurality of outwardly-facing, spaced-apart, segmented, annular ribs or lands for frictionally engaging the coronary sinus, each segmented annular rib or land comprising a plurality of solid, raised, generally elongate rib portions separated by non-raised portions extending annularly around the periphery of the balloon in alternating fashion, the non-raised portions preferentially stretching in comparison to the raised rib portions as the balloon is inflated to its inflated diameter, the balloon, including the ribs or lands, being integrally molded of generally uniform elastomeric material; and the raised rib portions having a generally asymmetrical profile along the longitudinal direction of the catheter, the raised rib portions having an upper surface sloping smoothly and gradually in the distal direction to the surface of the balloon, and a proximal surface extending from the upper surface more steeply to the surface of the balloon than the upper surface slopes to the surface of the balloon.

14. A coronary sinus catheter for the retrograde infusion of cardioplegia solution into the coronary sinus of a patient's heart, the catheter comprising:

a flexible, elongate catheter tube having proximal and distal ends and an outer diameter, and including at least an infusion lumen extending longitudinally through the tube, at least one infusion lumen outlet generally adjacent the distal end of the catheter tube, and means adjacent the proximal end of the catheter tube for connecting a source of cardioplegia solution to the catheter; and an inflatable balloon on the catheter tube generally adjacent the distal end of the catheter tube proximally of the infusion lumen outlet;

the inflatable balloon having a plurality of outwardly-facing, spaced-apart, segmented, annular ribs or lands for engaging the coronary sinus, each segmented annular rib or land comprising a plurality of solid, raised rib portions separated by non-raised portions extending annularly around the periphery of the balloon in alternating fashion;

wherein the raised rib portions have a generally asymmetrical profile along the longitudinal direction of the catheter, the raised rib portions having an upper surface sloping smoothly and gradually in the distal direction to the surface of the balloon, and a proximal surface extending from the upper surface more steeply to the surface of the balloon than the upper surface slopes to the surface of the balloon.

15. A coronary sinus catheter according to claim 14 wherein the raised rib portions are generally elongate having a direction of elongation extending generally circumferentially along the balloon.

16. A coronary sinus catheter according to claim 15 wherein the raised rib portions have a length along their direction of elongation longer than the distance between adjacent raised rib portions along the non-raised portion separating the adjacent raised rib portions.

17. A coronary sinus catheter according to claim 16 wherein the raised rib portions of one segmented rib or land each have a length along their direction of elongation generally equal to the other raised rib portions of that segmented rib or land.

18. A coronary sinus catheter according to claim 17 wherein the non-raised portions of one segmented rib or land each define a distance between adjacent raised rib portions generally equal to the distance between raised rib portions defined by the other non-raised portions of that segmented rib or land.

19. A coronary sinus catheter according to claim 18 wherein the catheter tube further defines a pressure lumen having lumen outlet generally adjacent the distal end of the catheter tube.

20. A coronary sinus catheter according to claim 19 wherein the balloon and rib portions are integrally formed of elastomeric material having a Shore A hardness of between approximately 20 and 35.

21. A coronary sinus catheter according to claim 20 wherein the balloon and rib portions are integrally formed of silicone material.

22. A coronary sinus catheter according to claim 15 wherein the raised rib portions of adjacent ribs or lands are staggered such that the raised rib portions of one rib or land are generally longitudinally aligned with the non-raised portions of the adjacent rib or land.

23. A coronary sinus catheter according to claim 15 wherein each segmented rib or land has the same number of raised rib portions and non-raised portions as the other ribs or lands.

24. A coronary sinus catheter according to claim 15 wherein the plurality of segmented ribs or lands comprises three to seven segmented ribs or lands.

25. A coronary sinus catheter according to claim 16 wherein the raised rib portions of adjacent ribs or lands are staggered such that the raised rib portions of one rib or land are generally longitudinally aligned with the non-raised portions of the adjacent rib or land.

26. A coronary sinus catheter according to claim 17 wherein the raised rib portions of adjacent ribs or lands are staggered such that the raised rib portions of one rib or land are generally longitudinally aligned with the non-raised portions of the adjacent rib or land.

27. A coronary sinus catheter according to claim 14 wherein the raised rib portions are generally elongate each having a length along its direction of elongation longer than the distance between adjacent raised rib portions along the non-raised portion separating the adjacent raised rib portions.

28. A coronary sinus catheter according to claim 27 wherein the raised rib portions of one segmented rib or land each have a length along their direction of elongation generally equal to the other raised rib portions of that segmented rib or land.

29. A coronary sinus catheter according to claim 28 wherein the non-raised portions of one segmented rib or land each define a distance between adjacent raised rib portions generally equal to the distance between raised rib portions defined by the other non-raised portions of that segmented rib or land.

30. A coronary sinus catheter according to claim 14 wherein the raised rib portions of one segmented rib or land are generally elongate, each rib portion having a length along its direction of elongation generally equal to the other raised rib portions of that segmented rib or land.

31. A coronary sinus catheter according to claim 30 wherein the plurality of segmented ribs or lands comprises three to seven segmented ribs or lands.

32. A coronary sinus catheter according to claim 30 wherein the non-raised portions of one segmented rib or land each define a distance between adjacent raised rib portions generally equal to the distance between raised rib portions defined by the other non-raised portions of that segmented rib or land.

33. A coronary sinus catheter according to claim 14 wherein the non-raised portions of one segmented rib or land each define a distance between adjacent raised rib portions generally equal to the distance between raised rib portions defined by the other non-raised portions of that segmented rib or land.

34. A coronary sinus catheter according to claim 33 wherein the raised rib portions of adjacent ribs or lands are staggered such that the raised rib portions of one rib or land are generally longitudinally aligned with the non-raised portions of the adjacent rib or land.

35. A coronary sinus catheter according to claim 14 wherein the catheter tube further defines a pressure lumen having lumen outlet generally adjacent the distal end of the catheter tube.

36. A coronary sinus catheter according to claim 35 wherein the balloon and rib portions are integrally formed of elastomeric material having a Shore A hardness of between approximately 20 and 35.

37. A coronary sinus catheter according to claim 35 wherein the raised rib portions of adjacent ribs or lands are staggered such that the raised rib portions of one rib or land are generally longitudinally aligned with the non-raised portions of the adjacent rib or land.

38. A coronary sinus catheter according to claim 14 wherein the balloon and rib portions are integrally formed of elastomeric material having a Shore A hardness of between approximately 20 and 35.

39. A coronary sinus catheter according to claim 14 wherein the balloon and rib portions are integrally formed of silicone material.

40. A coronary sinus catheter according to claim 14 wherein the plurality of segmented ribs or lands comprises three to seven segmented ribs or lands.

41. A coronary sinus catheter according to claim 40 wherein the plurality of segmented ribs or lands comprises six segmented ribs or lands.

42. A coronary sinus catheter according to claim 14 wherein each segmented rib or land has the same number of raised rib portions and non-raised portions as the other ribs or lands.

43. A coronary sinus catheter according to claim 14 wherein the raised rib portions of adjacent ribs or lands are staggered such that the raised rib portions of one rib or land are generally longitudinally aligned with the non-raised portions of the adjacent rib or land.

44. A coronary sinus catheter according to claim 14 wherein the balloon comprises a molded balloon having two tubular extensions that are glued to the catheter tube to mount the balloon on the catheter tube.

45. A coronary sinus catheter for the retrograde infusion of cardioplegia solution into the coronary sinus of a patient's heart, the catheter comprising:

a flexible, elongate catheter tube having proximal and distal ends and an outer diameter, and including at least an infusion lumen extending longitudinally through the tube, at least one infusion lumen outlet generally adjacent the distal end of the catheter tube, and means adjacent the proximal end of the catheter tube for connecting a source of cardioplegia solution to the catheter; and an inflatable balloon on the catheter tube generally adjacent the distal end of the catheter tube proximally of the infusion lumen outlet, the inflatable balloon being expandable as the balloon is inflated from an uninflated diameter, generally equal to the outer diameter of the catheter tube for introducing the catheter into the coronary sinus, to an inflated diameter, substantially greater than the outer diameter of the catheter tube for securing the distal end of the catheter in the coronary sinus;

the inflatable balloon having a plurality of outwardly-facing, spaced-apart, segmented, annular ribs or lands for engaging the coronary sinus, each segmented annular rib or land comprising a plurality of solid, raised, generally elongate rib portions separated by non-raised portions extending annularly around the periphery of the balloon in alternating fashion;

wherein the raised rib portions have a generally asymmetrical profile along the longitudinal direction of the catheter, the raised rib portions having an upper surface sloping smoothly and gradually in the distal direction to the surface of the balloon, and a proximal surface extending from the upper surface more steeply to the surface of the balloon than the upper surface slopes to the surface of the balloon.

46. A coronary sinus catheter according to claim 45 wherein the plurality of segmented ribs or lands comprises three to seven segmented ribs or lands.

47. A coronary sinus catheter according to claim 46 wherein each segmented rib or land has the same number of raised rib portions and non-raised portions as the other ribs or lands.

48. A coronary sinus catheter according to claim 45 wherein the raised rib portions of adjacent ribs or lands are staggered such that the raised rib portions of one rib or land are generally longitudinally aligned with the non-raised portions of the adjacent rib or land.

49. A coronary sinus catheter for the retrograde infusion of cardioplegia solution into the coronary sinus of a patient's heart, the catheter comprising:

a flexible, elongate catheter tube having proximal and distal ends and an outer diameter, and including at least an infusion lumen extending longitudinally through the tube, at least one infusion lumen outlet generally adjacent the distal end of the catheter tube, and means adjacent the proximal end of the catheter tube for connecting a source of cardioplegia solution to the catheter: and an inflatable balloon on the catheter tube generally adjacent the distal end of the catheter tube proximally of the infusion lumen outlet, the inflatable balloon being expandable as the balloon is inflated from an uninflated diameter, generally equal to the outer diameter of the catheter tube for introducing the catheter into the coronary sinus, to an inflated diameter, substantially greater than the outer diameter of the catheter tube for securing the distal end of the catheter in the coronary sinus;

the inflatable balloon having a plurality of outwardly-facing, spaced-apart, segmented, annular ribs or lands for engaging the coronary sinus, each segmented annular rib or land comprising a plurality of solid, raised, generally elongate rib portions separated by non-raised portions extending annularly around the periphery of the balloon in alternating fashion;

the balloon comprising a molded balloon having two tubular extensions that are glued to the catheter tube to mount the balloon on the catheter tube; and the tubular extensions including annular ribs extending radially inwardly adjacent the expandable portion of the balloon to provide an even glue line adjacent the expandable portion of the balloon.

50. A coronary sinus catheter according to claim 49 wherein the raised rib portions have a generally asymmetrical profile along the longitudinal direction of the catheter, the raised rib portions having an upper surface sloping smoothly and gradually in the distal direction to the surface of the balloon, and a proximal surface extending from the upper surface more steeply to the surface of the balloon than the upper surface slopes to the surface of the balloon.

51. A coronary sinus catheter according to claim 50 wherein the plurality of segmented ribs or lands comprises three to seven segmented ribs or lands.

52. A coronary sinus catheter according to claim 51 wherein each segmented rib or land has the same number of raised rib portions and non-raised portions as the other ribs or lands.

53. A coronary sinus catheter according to claim 51 wherein the raised rib portions of adjacent ribs or lands are staggered such that the raised rib portions of one rib or land are generally longitudinally aligned with the non-raised portions of the adjacent rib or land.

54. A coronary sinus catheter according to claim 49 wherein the raised rib portions of adjacent ribs or lands are staggered such that the raised rib portions of one rib or land are generally longitudinally aligned with the non-raised portions of the adjacent rib or land.

55. A coronary sinus catheter for the retrograde infusion of cardioplegia solution into the coronary sinus of a patient's heart, the catheter comprising:

a flexible, elongate catheter tube having proximal and distal ends and an outer diameter, and including at least an infusion lumen extending longitudinally through the tube, at least one infusion lumen outlet generally adjacent the distal end of the catheter tube, and means adjacent the proximal end of the catheter tube for connecting a source of cardioplegia solution to the catheter; and an inflatable balloon on the catheter tube generally adjacent the distal end of the catheter tube proximally of the infusion lumen outlet, the inflatable balloon being expandable as the balloon is inflated from an uninflated diameter, generally equal to the outer diameter of the catheter tube for introducing the catheter into the coronary sinus, to an inflated diameter, substantially greater than the outer diameter of the catheter tube for securing the distal end of the catheter in the coronary sinus;

the inflatable balloon having a plurality of outwardly-facing, spaced-apart, segmented, annular ribs or lands for engaging the coronary sinus, each segmented annular rib or land comprising a plurality of solid, raised, generally elongate rib portions separated by non-raised portions extending annularly around the periphery of the balloon in alternating fashion;

wherein the generally elongate raised rib portions have a direction of elongation extending generally circumferentially along the balloon, the raised rib portions having a length along their direction of elongation longer than the distance between adjacent raised rib portions along the non-raised portion separating the adjacent raised rib portions;

the raised rib portions of one segmented rib or land each have a length along their direction of elongation generally equal to the other raised rib portions of that segmented rib or land;

the non-raised portions of one segmented rib or land each defining a distance between adjacent raised rib portions generally equal to the distance between raised rib portions defined by the other non-raised portions of that segmented rib or land;

the catheter tube further defining a pressure lumen having lumen outlet generally adjacent the distal end of the catheter tube;

the balloon and rib portions are integrally formed of elastomeric silicone material having a Shore A hardness of between approximately 20 and 35;

wherein the raised rib portions have a generally asymmetrical profile along the longitudinal direction of the catheter, the raised rib portions having an upper surface sloping smoothly and gradually in the distal direction to the surface of the balloon, and a proximal surface extending from the upper surface more steeply to the surface of the balloon than the upper surface slopes to the surface of the balloon;

the plurality of segmented ribs or lands comprising three to seven segmented ribs or lands;

the balloon comprising a molded balloon having two tubular extensions that are glued to the catheter tube to mount the balloon on the catheter tube; and the tubular extensions including annular ribs extending radially inwardly adjacent the expandable portion of the balloon to provide an even glue line adjacent the expandable portion of the balloon.

56. A coronary sinus catheter assembly for the retrograde infusion of cardioplegia solution into the coronary sinus of a patient's heart, the catheter assembly comprising:

a catheter comprising:

a flexible, elongate catheter tube having proximal and distal ends and an outer diameter, and including at least an infusion lumen extending longitudinally through the tube, at least one infusion lumen outlet generally adjacent the distal end of the catheter tube, and means adjacent the proximal end of the catheter tube for connecting a source of cardioplegia solution to the catheter; and an inflatable balloon on the catheter tube generally adjacent the distal end of the catheter tube proximally of the infusion lumen outlet;

the inflatable balloon having a plurality of outwardly-facing, spaced-apart, segmented, annular ribs or lands for engaging the coronary sinus, each segmented annular rib or land comprising a plurality of solid, raised rib portions separated by non-raised portions extending annularly around the periphery of the balloon in alternating fashion, the raised rib portions of adjacent ribs or lands are staggered such that the raised rib portions of one rib or land are generally longitudinally aligned with the non-raised portions of the adjacent rib or land; and a stylet removably received in the infusion lumen of the catheter.

57. A coronary sinus catheter assembly according to claim 56 wherein the raised rib portions are generally elongate having a direction of elongation extending generally circumferentially along the balloon.

58. A coronary sinus catheter assembly according to claim 57 wherein the raised rib portions have a length along their direction of elongation longer than the distance between adjacent raised rib portions along the non-raised portion separating the adjacent raised rib portions.

59. A coronary sinus catheter assembly according to claim 58 wherein the raised rib portions of one segmented rib or land each have a length along their direction of elongation generally equal to the other raised rib portions of that segmented rib or land.

60. A coronary sinus catheter assembly according to claim 59 wherein the non-raised portions of one segmented rib or land each define a distance between adjacent raised rib portions generally equal to the distance between raised rib portions defined by the other non-raised portions of that segmented rib or land.

61. A coronary sinus catheter assembly according to claim 60 wherein the catheter tube further defines a pressure lumen having lumen outlet generally adjacent the distal end of the catheter tube.

62. A coronary sinus catheter assembly according to claim 61 wherein the balloon and rib portions are integrally formed of elastomeric material having a Shore A hardness of between approximately 20 and 35.

63. A coronary sinus catheter assembly according to claim 61 wherein the raised rib portions have a generally asymmetrical profile along the longitudinal direction of the catheter, the raised rib portions having an upper surface sloping smoothly and gradually in the distal direction to the surface of the balloon, and a proximal surface extending from the upper surface more steeply to the surface of the balloon than the upper surface slopes to the surface of the balloon.

64. A coronary sinus catheter assembly according to claim 56 wherein the catheter tube further defines a pressure lumen having lumen outlet generally adjacent the distal end of the catheter tube.

65. A coronary sinus catheter assembly according to claim 56 wherein the balloon and rib portions are integrally formed of elastomeric material having a Shore A hardness of between approximately 20 and 35.

66. A coronary sinus catheter assembly according to claim 65 wherein the balloon and rib portions are integrally formed of silicone material.

67. A coronary sinus catheter assembly according to claim 66 wherein the raised rib portions have a generally asymmetrical profile along the longitudinal direction of the catheter, the raised rib portions having an upper surface sloping smoothly and gradually in the distal direction to the surface of the balloon, and a proximal surface extending from the upper surface more steeply to the surface of the balloon than the upper surface slopes to the surface of the balloon.

68. A coronary sinus catheter assembly according to claim 56 wherein the balloon and rib portions are integrally formed of silicone material.

69. A coronary sinus catheter assembly according to claim 56 wherein the raised rib portions have a generally asymmetrical profile along the longitudinal direction of the catheter, the raised rib portions having an upper surface sloping smoothly and gradually in the distal direction to the surface of the balloon, and a proximal surface extending from the upper surface more steeply to the surface of the balloon than the upper surface slopes to the surface of the balloon.

70. A coronary sinus catheter assembly according to claim 69 wherein the plurality of segmented ribs or lands comprises three to seven segmented ribs or lands.

71. A coronary sinus catheter assembly according to claim 70 wherein each segmented rib or land has the same number of raised rib portions and non-raised portions as the other ribs or lands.

72. A coronary sinus catheter assembly according to claim 56 wherein the plurality of segmented ribs or lands comprises three to seven segmented ribs or lands.

73. A coronary sinus catheter assembly according to claim 56 wherein each segmented rib or land has the same number of raised rib portions and non-raised portions as the other ribs or lands.

74. A coronary sinus catheter assembly according to claim 56 wherein the balloon comprises a molded balloon having two tubular extensions that are glued to the catheter tube to mount the balloon on the catheter tube.

75. A coronary sinus catheter assembly for the retrograde infusion of cardioplegia solution into the coronary sinus of a patient's heart, the catheter assembly comprising:

a catheter comprising:

a flexible, elongate catheter tube having proximal and distal ends and an outer diameter, and including at least an infusion lumen extending longitudinally through the tube, at least one infusion lumen outlet generally adjacent the distal end of the catheter tube, and means adjacent the proximal end of the catheter tube for connecting a source of cardioplegia solution to the catheter; and an inflatable balloon on the catheter tube generally adjacent the distal end of the catheter tube proximally of the infusion lumen outlet, the inflatable balloon being expandable as the balloon is inflated from an uninflated diameter, generally equal to the outer diameter of the catheter tube for introducing the catheter into the coronary sinus, to an inflated diameter, substantially greater than the outer diameter of the catheter tube for securing the distal end of the catheter in the coronary sinus;

the inflatable balloon having a plurality of outwardly-facing, spaced-apart, segmented, annular ribs or lands for engaging the coronary sinus, each segmented annular rib or land comprising a plurality of solid, raised, generally elongate rib portions separated by non-raised portions extending annularly around the periphery of the balloon in alternating fashion, the raised rib portions of adjacent ribs or lands being staggered such that the raised rib portions of one rib or land are generally longitudinally aligned with the non-raised portions of the adjacent rib or land; and a stylet removably received in the infusion lumen of the catheter.

76. A coronary sinus catheter assembly according to claim 75 wherein the raised rib portions have a generally asymmetrical profile along the longitudinal direction of the catheter, the raised rib portions having an upper surface sloping smoothly and gradually in the distal direction to the surface of the balloon, and a proximal surface extending from the upper surface more steeply to the surface of the balloon than the upper surface slopes to the surface of the balloon.

77. A coronary sinus catheter assembly for the retrograde infusion of cardioplegia solution into the coronary sinus of a patient's heart, the catheter assembly comprising:

a catheter comprising:

a flexible, elongate catheter tube having proximal and distal ends and an outer diameter, and including at least an infusion lumen extending longitudinally through the tube, at least one infusion lumen outlet generally adjacent the distal end of the catheter tube, and means adjacent the proximal end of the catheter tube for connecting a source of cardioplegia solution to the catheter; and an inflatable balloon on the catheter tube generally adjacent the distal end of the catheter tube proximally of the infusion lumen outlet, the inflatable balloon being expandable as the balloon is inflated from an uninflated diameter, generally equal to the outer diameter of the catheter tube for introducing the catheter into the coronary sinus, to an inflated diameter, substantially greater than the outer diameter of the catheter tube for securing the distal end of the catheter in the coronary sinus;

the inflatable balloon having a plurality of outwardly-facing, spaced-apart, segmented, annular ribs or lands for engaging the coronary sinus, each segmented annular rib or land comprising a plurality of solid, raised, generally elongate rib portions separated by non-raised portions extending annularly around the periphery of the balloon in alternating fashion; and a stylet removably received in the infusion lumen of the catheter;

the balloon comprising a molded balloon having two tubular extensions that are glued to the catheter tube to mount the balloon on the catheter tube; and the tubular extensions including annular ribs extending radially inwardly adjacent the expandable portion of the balloon to provide an even glue line adjacent the expandable portion of the balloon.

78. A coronary sinus catheter assembly according to claim 77 wherein the raised rib portions of adjacent ribs or lands are staggered such that the raised rib portions of one rib or land are generally longitudinally aligned with the non-raised portions of the adjacent rib or land.

79. A cardiovascular catheter comprising:

a flexible, elongate catheter tube having proximal and distal ends and an outer diameter, and including at least an infusion lumen extending longitudinally through the tube, at least one infusion lumen outlet generally adjacent the distal end of the catheter tube, and means adjacent the proximal end of the catheter tube for connecting a source of fluid to the catheter; and an inflatable balloon on the catheter tube generally adjacent the distal end of the catheter tube proximally of the infusion lumen outlet;

the inflatable balloon having a plurality of outwardly-facing, spaced-apart, segmented, annular ribs or lands for engaging the internal walls of a blood vessel, each segmented annular rib or land comprising a plurality of solid, raised, generally elongate rib portions separated by non-raised portions extending circumferentially around the periphery of the balloon in alternating fashion, the raised rib portions having a direction of elongation extending generally circumferentially along the balloon, the balloon, including the ribs or lands, being integrally molded of generally uniform elastomeric material.

80. A cardiovascular catheter according to claim 79 wherein each raised rib portion has a length along its direction of elongation longer than the distance between adjacent raised rib portions along the non-raised portion separating the adjacent raised rib portions.

81. A cardiovascular catheter according to claim 80 further comprising a pressure sensing lumen within the catheter tube separate from the infusion lumen.

82. A cardiovascular catheter according to claim 80 further comprising two separate lumens in addition to the infusion lumen, one of the separate lumens comprising a balloon inflation lumen in fluid communication with the balloon to inflate and deflate the balloon.

83. A cardiovascular catheter according to claim 82 wherein the raised rib portions of adjacent ribs or lands are staggered such that the raised rib portions of one rib or land are generally longitudinally aligned with the non-raised portions of the adjacent rib or land.

84. A cardiovascular catheter according to claim 83 wherein the raised rib portions have a generally asymmetrical profile along the longitudinal direction of the catheter, the raised rib portions having an upper surface sloping smoothly and gradually in the distal direction to the surface of the balloon, and a proximal surface extending from the upper surface more steeply to the surface of the balloon than the upper surface slopes to the surface of the balloon.

85. A cardiovascular catheter comprising:

a flexible, elongate catheter tube having proximal and distal ends and an outer diameter, and including at least an infusion lumen extending longitudinally through the tube, at least one infusion lumen outlet generally adjacent the distal end of the catheter tube, and means adjacent the proximal end of the catheter tube for connecting a source of fluid to the catheter; and an inflatable balloon on the catheter tube generally adjacent the distal end of the catheter tube proximally of the infusion lumen outlet, the inflatable balloon having a plurality of outwardly-facing, spaced-apart, segmented, annular ribs or lands for engaging the internal walls of a blood vessel, each segmented annular rib or land comprising a plurality of solid, raised rib portions separated by non-raised portions extending annularly around the periphery of the balloon in alternating fashion;

the balloon comprising an expandable portion and two tubular extensions extending from opposite ends of the expandable portion, the tubular extensions being glued to the catheter tube to mount the expandable portion of the balloon on the catheter tube, the tubular extensions including annular ribs extending radially inwardly adjacent the expandable portion of the balloon to provide an even glue line adjacent the expandable portion of the balloon.

* * * * *

UNITED STATES PATENT AND TRADEMARK OFFICE
CERTIFICATE OF CORRECTION

PATENT NO. : 5,620,418
DATED : April 15, 1997
INVENTOR(S) : William G. O'Neill, Nelson L. Huldin, Sheila J. Hanson and Walter L. Carpenter It is certified that error appears in the above-identified patent and that said Letters Patent is hereby corrected as shown below:

Title Page (Page 2) "OTHER PUBLICATIONS" please delete the second occurrence of the following reference "Zombolas et al.; "Retrograde coronary sinus perfusion: pressure monitoring"; Perfusion 1992; 7:291-294." and add the following reference in its place --Menasche et al.; "Retrograde Coronary Sinus Perfusion: A Safe Alternative for Ensuring Cardioplegic Delivery in Aortic Valve Surgery"; The Annals of Thoracic Surgery, Vol. 34, No. 6, December 1982"--.

Col. 14, line 16, "1" should read --5--.
Col. 18, line 38, "catheter:" should read --catheter;--.

Signed and Sealed this

Fourteenth Day of April, 1998

Attest:

BRUCE LEHMAN

Attesting Officer

Commissioner of Patents and Trademarks